(12) United States Patent
Halpaap et al.

(10) Patent No.: US 9,376,403 B2
(45) Date of Patent: Jun. 28, 2016

(54) PROCESS FOR TRIMERISING CYCLOALIPHATIC DIISOCYANATES

(71) Applicant: Bayer MaterialScience AG, Leverkusen (DE)

(72) Inventors: Reinhard Halpaap, Odenthal (DE); Mario Schneider, Odenthal (DE); Oswald Wilmes, Köln (DE); Uwe Werner, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 131 days.

(21) Appl. No.: 13/971,018

(22) Filed: Aug. 20, 2013

(65) Prior Publication Data

US 2014/0058102 A1    Feb. 27, 2014

(30) Foreign Application Priority Data

Aug. 23, 2012 (EP) .................... 12181517

(51) Int. Cl.
| | |
|---|---|
| C07D 251/34 | (2006.01) |
| C08G 18/75 | (2006.01) |
| C08G 18/02 | (2006.01) |
| C08G 18/09 | (2006.01) |
| C08G 18/18 | (2006.01) |

(52) U.S. Cl.
CPC ............ C07D 251/34 (2013.01); C08G 18/022 (2013.01); C08G 18/092 (2013.01); C08G 18/1875 (2013.01); C08G 18/755 (2013.01)

(58) Field of Classification Search
CPC .. C07D 251/34; C08G 18/022; C08G 18/092; C08G 18/755; C08G 18/1875

USPC ......................................................... 544/221
See application file for complete search history.

(56) References Cited

U.S. PATENT DOCUMENTS

| | | | |
|---|---|---|---|
| 4,288,586 | A | 9/1981 | Bock et al. |
| 6,452,003 | B1 | 9/2002 | Ewald et al. |
| 8,119,799 | B2 | 2/2012 | Binder et al. |

FOREIGN PATENT DOCUMENTS

| | | |
|---|---|---|
| DE | 10 2004 060131 A1 | 6/2006 |
| EP | 0003765 A1 | 9/1979 |
| EP | 0524501 A1 | 1/1993 |
| EP | 1170283 A2 | 1/2002 |
| WO | WO-2005/087828 A1 | 9/2005 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
European Search Report dated Jan. 17, 2013 in corresponding European Patent Application No. 12181517.9.

* cited by examiner

*Primary Examiner* — James O Wilson
*Assistant Examiner* — Ebenezer O Sackey
(74) *Attorney, Agent, or Firm* — Drinker Biddle & Reath LLP

(57) ABSTRACT

The invention relates to a process for preparing polyisocyanates containing isocyanurate groups by trimerising cycloaliphatic diisocyanates using a catalyst solution comprising at least one quaternary ammonium hydroxide, characterized in that the catalyst solution is metered in such that the reaction temperature is >90° C. and ≤140° C.

23 Claims, No Drawings

PROCESS FOR TRIMERISING CYCLOALIPHATIC DIISOCYANATES

RELATED APPLICATIONS

This application claims benefit of European application 12181517.9, filed Aug. 23, 2012, which is incorporated herein by reference in its entirety for all its useful purposes.

FIELD OF THE INVENTION

The invention relates to a process for preparing polyisocyanates containing isocyanurate groups by trimerising cycloaliphatic diisocyanates using a catalyst solution comprising at least one quaternary ammonium hydroxide.

BACKGROUND OF THE INVENTION

Low-monomer content polyisocyanates have been used for some decades as useful hardeners for polyurethane coatings and adhesives.

These hardeners are generally prepared from diisocyanates. The modification of these diisocyanates to give polyisocyanates is particularly advantageous for two predominant reasons. Firstly, mainly branches are introduced by the modification, such that the polyisocyanates usually have NCO functionalities >2, often in the range of 2.4 to 4.5, and so are particularly well suited to the formation of highly cross-linked, very durable coatings. However, even for a solely linear modification, such as the reaction with diols to give linear prepolymers, the hardeners obtained are "given" particular properties, such as the ability to achieve particularly flexible coatings. Secondly, following the actual modification of the diisocyanates, in many cases the excess monomeric diisocyanate is removed and fed back into the modification process. The polyisocyanates have a vapour pressure an order of magnitude lower than the quite volatile diisocyanates, such that they are distinctly less physiologically active and are considerably easier to handle from an occupational hygiene point of view.

Diisocyanates used industrially in large quantities are toluene diisocyanate (TDI), diphenylmethane diisocyanate (MDI), hexamethylene diisocyanate (HDI), isophorone diisocyanate (IPDI) and dicyclohexylmethane diisocyanate ($H_{12}$-MDI). In addition to these industrially available diisocyanates, further diisocyanates are available in industrial quantities. These are described, for example, in addition to the diisocyanates explicitly mentioned above, in Ullmann (Christian Six, Frank Richter, 2005 Wiley-VCH Verlag GmbH & Co. KGaA, Weinheim 10.1002/14356007.a14_611) and frequently have the character of specialty isocyanates for very particular applications.

Aromatic diisocyanates, in which the NCO groups are bonded directly to an aromatic ring, such as TDI and MDI, are distinguished from aliphatic diisocyanates having isocyanatoalkyl groups, such as HDI, IPDI and $H_{12}$-MDI. For high-quality lightfast coatings, the latter are of particular interest since they afford non-yellowing colour-stable coatings.

The oligomerisation of diisocyanates to polyisocyanates is known and has been described many times; for example, see H. J. Laas et al. in J. Prakt. Chem. 336 (1994), 185ff. The oligomerization methods described generally differ in the selection of the diisocyanates used, the selection of the catalysts and the choice of the specific reaction conditions.

The diisocyanate is typically placed in the reaction vessel and pre-heated to, or to slightly below, the reaction temperature. The catalyst solution suitable for the trimerisation is then added continuously over a certain time period. After the reaction commences ("onset" of the reaction), the strongly exothermic reaction is normally cooled and, by regulating the metered addition of the catalyst and cooling, the reaction is conducted so that the desired target NCO content of the crude solution is achieved. By addition of a chemical stopper, catalyst still present is deactivated. The oligomeric polyisocyanate is separated from excess monomeric diisocyanate in a subsequent process step. This separation is generally effected by distillation in suitable apparatuses, preferably by multistage distillation including at least one thin-film distillation.

EP-A 0003765 describes the trimerisation of IPDI using quaternary hydroxyalkyl-substituted ammonium hydroxides as catalysts at reaction temperatures of 30 to 90° C.

This reaction procedure is unfavourable since catalyst salts which form during and after the reaction are not fully soluble at reaction temperatures below 90° C., particularly in the case of the cycloaliphatic diisocyanates used here and quaternary ammonium hydroxide compounds used as catalysts and the acidic chemical stoppers. These salts, which appear in the form of turbidity, interfere with the heat transfer by covering reactor walls and cooling surfaces of the heat exchangers and necessitate frequent cleaning of the apparatuses. The quaternary ammonium hydroxide compounds used as catalysts are themselves thermolabile and are broken down at elevated temperatures; see, for example, H. J. Laas et al. in J. Prakt. Chem. 336 (1994), 185ff. In this case, the anion of the salt is alkylated and cleared into tertiary amines. Some of the decomposition products are volatile and some form salts which are in turn no longer catalytically active.

The object of the present invention, therefore, was to provide a discontinuous (batch) or continuous process in which the trimerisation of cycloaliphatic diisocyanates, catalysed by ammonium hydroxide compounds, is carried out such that deposition of solids that interfere with the operation of the plant does not occur in the apparatuses. In particular, the specific process shall ensure a long operating time without disruptions and costly downtime and without necessitating frequent cleaning operations. Moreover, compared to the trimerisation at a temperature below 90° C., no significantly higher catalyst requirement should occur.

EMBODIMENTS OF THE INVENTION

An embodiment of the present invention is a process for preparing a polyisocyanate containing isocyanurate groups comprising trimerising a cycloaliphatic diisocyanate in the presence of a catalyst solution comprising at least one quaternary ammonium hydroxide in a reaction solution, wherein the catalyst solution is metered in to said reaction solution such that a reaction temperature of >90° C. and ≤140° C. is maintained.

Another embodiment of the present invention is the above process, wherein the catalyst solution is metered in to said reaction solution such that a reaction temperature of >90° C. and ≤135° C. is maintained.

Another embodiment of the present invention is the above process, wherein the catalyst solution is metered in to said reaction solution such that a reaction temperature of >90° C. and ≤120° C. is maintained.

Another embodiment of the present invention is the above process, wherein the process is carried out continuously in one or more stirred tanks.

Another embodiment of the present invention is the above process, wherein an NCO content is achieved corresponding to a degree of trimerisation of from 8 to 30%.

Another embodiment of the present invention is the above process, wherein an NCO content is achieved corresponding to a degree of trimerisation of from 12 to 24%.

Yet another embodiment of the present invention is a continuous process for preparing a polyisocyanate containing isocyanurate groups comprising trimerising a cycloaliphatic diisocyanate in the presence of a catalyst solution comprising at least one quaternary ammonium hydroxide in a stirred tank cascade with n stirred tanks, wherein, in at least n/2 or (n/2−0.5) tanks, the metered addition is such that the reaction temperature in at least n/2 or (n/2+0.5) tanks is >90° C. and ≤140° C., where n/2 applies to an even number of tanks and (n/2−0.5) or (n/2+0.5) applies to an odd number of tanks and n is a whole number from 2 to 6.

Another embodiment of the present invention is the above continuous process, wherein an NCO content is achieved in the nth tank corresponding to a degree of trimerisation of from 8 to 30%.

Another embodiment of the present invention is the above continuous process, wherein an NCO content is achieved in the nth tank corresponding to a degree of trimerisation of from 12 to 24%.

Another embodiment of the present invention is the above process, wherein the catalyst comprises from 0.001 to 2% by weight of quaternary ammonium hydroxide, based on the amount of diisocyanate.

Another embodiment of the present invention is the above process, wherein the catalyst comprises from 0.005 to 1% by weight of quaternary ammonium hydroxide, based on the amount of diisocyanate.

Another embodiment of the present invention is the above process, wherein the catalyst solution has a catalyst concentration of from 0.1 to 10% by weight, based on the catalyst solution.

Another embodiment of the present invention is the above process, wherein the catalyst solution has a catalyst concentration of from 0.2 to 8% by weight, based on the catalyst solution.

Another embodiment of the present invention is the above process, wherein the catalyst solution comprises at least one quaternary tetraalkylammonium hydroxide and/or a mixed quaternary tetraalkyl/aralkylammonium hydroxide and/or a quaternary tetraaralkylammonium hydroxide.

Another embodiment of the present invention is the above process, wherein the catalyst solution comprises at least one quaternary trialkylaralkylammonium hydroxide.

Another embodiment of the present invention is the above process, wherein the catalyst solution comprises at least one quaternary tetraalkylammonium hydroxide and/or one quaternary mixed tetraalkyl/aralkylammonium hydroxide, wherein the alkyl groups of said at least one quaternary tetraalkylammonium hydroxide and/or one quaternary mixed tetraalkyl/aralkylammonium hydroxide are not substituted with any hydroxyl groups.

Another embodiment of the present invention is the above process, wherein the catalyst comprises a quaternary benzyltrialkylammonium hydroxide.

Another embodiment of the present invention is the above process, wherein the catalyst solution comprises benzyltrimethylammonium hydroxide.

Another embodiment of the present invention is the above process, wherein the cycloaliphatic diisocyanate comprises IPDI.

Another embodiment of the present invention is the above process, wherein the trimerization is stopped chemically or thermally.

Another embodiment of the present invention is the above process, wherein the trimerization is stopped chemically by adding an acidic compound, an acid, and/or an alkylating agent to the reaction solution.

Another embodiment of the present invention is the above process, further comprising, in a downstream step, removing monomeric cycloaliphatic diisocyanate still present from the polyisocyanate by distillation.

Another embodiment of the present invention is the above process, wherein the reaction solution is stopped thermally.

DETAILED DESCRIPTION OF THE INVENTION

The object is achieved in accordance with the invention by a process for preparing polyisocyanates containing isocyanurate groups by trimerising cycloaliphatic diisocyanates using a catalyst solution comprising at least one quaternary ammonium hydroxide, characterized in that the catalyst solution is metered in such that the reaction temperature is >90° C. and ≤140° C.

It has surprisingly been found that, despite the strongly exothermic trimerisation reaction, external cooling of the reaction mixture can be largely dispensed with and the reaction can be carried out with good controllability at temperatures >90° C. and ≤140° C. It is particularly surprising that, despite the relatively high reaction temperature, the thermally labile quaternary ammonium catalyst catalyses the reaction sufficiently well to achieve the desired NCO content and, at the termination of the reaction, is rapidly thermally deactivated such that a stable crude solution is obtained without any further creeping drop in NCO. No significantly higher catalyst requirement is observed compared with trimerisation at a lower temperature below 90° C. (e.g. at 60-70° C.). Above 140° C., excessive deactivation of the catalyst occurs such that a considerably higher amount of catalyst is necessary to achieve the desired degree of trimerisation, or the reaction does not start at all due to the rapid catalyst decomposition.

It has been found that the reaction temperature should optimally be selected to be >90° C. and ≤140° C., preferably >90° C. and ≤135° C. and particularly preferably 95° C. and ≤120° C.

At this temperature, the catalyst is sufficiently stable to sustain the progress of the trimerisation without the thermal decomposition of the catalyst described above having a significant influence. Secondly, the reaction temperature selected is so high that clear, or only minimally cloudy, polyisocyanate solutions are obtained, in which salt deposits from catalyst decomposition products do not occur, or only to a very minor extent, on heat exchangers, reactor walls or pipelines.

This observation is surprising since the small temperature difference from a conventional reaction temperature of, for example, 70° C., as is typically selected for a sufficiently high reaction rate, is not expected to have such a drastic effect.

The salt deposits are surprisingly also avoided or suppressed to a minimum when diisocyanates are used having quite elevated contents of hydrolysable chloro compounds (HC contents) of, for example, >150-500 ppm, as can occur in diisocyanates obtained by phosgenation of diamines.

The process can be carried out as a batch process or continuously in one or more stirred tanks; preferably, it is carried out continuously in one or more stirred tanks.

The process according to the invention preferably achieves an NCO content corresponding to a degree of trimerisation of 8 to 30%, preferably 12 to 24%.

The stated degree of trimerisation ($T_g$) is understood to mean the proportion of NCO groups ($NCO_0$) present in the original diisocyanate which has been reacted during the oligomerisation. $T_g=(NCO_0-NCO)/NCO_0$, where the NCO value is the NCO content present in the current crude trimerisate solution.

The invention further provides a continuous process for preparing polyisocyanates containing isocyanurate groups by trimerising cycloaliphatic diisocyanates using a catalyst solution comprising at least one quaternary ammonium hydroxide in a stirred tank cascade with n stirred tanks, characterized in that, in at least n/2 or (n/2−0.5) tanks, the metered addition is such that the reaction temperature in at least n/2 or (n/2+0.5) tanks is >90° C. and ≤140° C., preferably >90° C. and ≤135° C. and particularly preferably ≥95° C. and ≤120° C., where n/2 applies an even number of tanks and (n/2−0.5) or (n/2+0.5) applies to an odd number of tanks and n is a whole number from 2 to 6.

In the present process according to the invention, an NCO content is preferably achieved in the nth tank corresponding to a degree of trimerisation of 8 to 30%, preferably 12 to 24%.

Catalysts particularly suitable for the process according to the present invention are the quaternary ammonium hydroxide compounds known to be very active catalysts (see H. J. Laas et al. in J. Prakt. Chem. 336 (1994), 185ff). Particularly suitable as catalysts are quaternary tetraalkylammonium hydroxides, mixed tetraalkyl/aralkylammonium hydroxides and tetraaralkylammonium hydroxides. Especially suitable are quaternary trialkylaralkylammonium hydroxides, such as benzyltrialkylammonium hydroxides. Also of good suitability are hydroxyalkyl-substituted quaternary ammonium hydroxides of the choline type.

The catalyst used is preferably at least one quaternary tetraalkylammonium hydroxide and/or one quaternary trialkylaralkylammonium hydroxide, preferably at least one quaternary trialkylaralkylammonium hydroxide. In a specific embodiment of the invention, a tetraalkylammonium hydroxide or a quaternary trialkylaralkylammonium hydroxide is used exclusively as catalyst, preferably exclusively a quaternary trialkylaralkylammonium hydroxide.

Especially preferably, at least one quaternary benzyltrialkylammonium hydroxide is used as catalyst.

Particular preference is given to using exclusively a quaternary benzyltrialkylammonium hydroxide, very particular preference to using exclusively benzyltrimethylammonium hydroxide.

In a further preferred embodiment of the invention, at least one quaternary tetraalkylammonium hydroxide and/or quaternary mixed tetraalkyl/aralkylammonium hydroxide is used as catalyst, the alkyl radicals of which do not comprise any hydroxyl groups.

The catalysts are generally used in amounts of 0.001-2% by weight, preferably 0.005-1% by weight and particularly preferably 0.005-0.2% by weight, based on the amount of diisocyanate used. The amounts specified refer to the active catalyst itself, i.e. the particular quaternary ammonium hydroxide used. The catalysts can be used either in pure form or preferably in dissolved form as described above, alcohols as solvents being known to act co-catalytically.

The alcohols preferred as catalyst solvents are any aliphatic alcohols, preferably low molecular weight mono or diols. Examples of catalyst solvents include: methanol, ethanol, isopropanol, n-butanol, 2-ethylhexanol, 1,2-dihydroxyethane, 1,2-dihydroxypropane, 1,3- and 1,4-dihydroxybutane, 1,6- and 2,5-dihydroxyhexane, or 2,2,4-trimethyl-1,3-dihydroxypentane or 2-ethyl-1,3-dihydroxyhexane or any mixtures of these alcohols.

The catalysts are used at concentrations of 0.1-10% by weight, preferably 0.2-8% by weight, especially preferably 1-5% by weight, based in each case on the catalyst solution, unless they are used solvent-free, which is less preferred.

For the process according to the invention, suitable cycloaliphatic diisocyanates are, for example, those in a molecular weight range of 166 to 318 g/mol, such as 1,3- or 1,4-diisocyanatocyclohexane, 1,4-diisocyanato-3,3,5-trimethylcyclohexane, 1,3-diisocyanato-2(4)-methylcyclohexane, 1-isocyanato-3,3,5-trimethyl-5-isocyanatomethylcyclohexane (isophorone diisocyanate, IPDI), 1-isocyanato-1-methyl-4(3)-isocyanato-methylcyclohexane, 1,8-diisocyanato-p-menthane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 4,4'- and/or 2,4'-diisocyanatodicyclohexylmethane, 4,4'-diisocyanato-3,3'-dimethyldicyclohexylmethane, 4,4'-diisocyanato-3,3',5,5'-tetramethyldicyclohexylmethane, 1,3-diisocyanatoadamantane, and 1,3-dimethyl-5,7-diisocyanatoadannantane, and also any mixtures of such diisocyanates. The manner in which the diisocyanates were prepared is unimportant. This can be effected by phosgenation of the diamines in the liquid phase or in the gas phase, but also equally by known phosgene-free processes such as thermal urethane cleavage with or without catalysis.

Preferred cycloaliphatic diisocyanates for the process according to the invention are IPDI and/or 4,4'- and/or 2,4'-diisocyanatodicyclohexylmethane. IPDI is especially preferably used.

The reaction solution can be stopped chemically or thermally, but is preferably stopped thermally.

In the case of chemical stopping, the reaction solution is stopped by addition of an acidic compound, an acid and/or an alkylating agent.

The preferred thermal stopping is conducted either at the selected reaction temperature by simple continuation of stirring after the reaction subsides or by raising the temperature by up to 50° C. and continuing to stir at this temperature.

The stopping temperature is preferably slightly raised by up to 20° C. compared to the reaction temperature. The thermal stopping is particularly preferably carried out at reaction temperature.

After termination of the trimerisation reaction, a solution of the isocyanurate group-containing polyisocyanate in excess monomeric cycloaliphatic diisocyanate is present as reaction product.

In a preferred embodiment of the invention, in a downstream step, monomeric cycloaliphatic diisocyanate still present is removed from this reaction mixture by distillation. This is carried out preferably by thin film distillation under reduced pressure, for example at a pressure of below 1.0 mbar, preferably below 0.5 mbar, particularly preferably below 0.2 mbar, under the mildest possible conditions, for example at a temperature of 100 to 200° C., preferably 120 to 180° C. The removal of the monomeric diisocyanate can be carried out in a single stage but preferably in more than one stage. Thus, a falling-film evaporator, for example, is used as a pre-evaporator, in which the majority of the monomeric diisocyanate is removed, and in a downstream thin film evaporator the removal of further starting diisocyanate is carried out. In this manner, high-quality polyisocyanates are obtained having a free diisocyanate content of not more than 0.5% by weight, preferably not more than 0.3% by weight. The distillates obtained are used again for the trimerisation.

In a further embodiment, the monomeric cycloaliphatic diisocyanates are removed from the reaction product by extraction using suitable solvents inert towards isocyanate groups, for example aliphatic or cycloaliphatic hydrocarbons such as pentane, hexane, heptane, cyclopentane or cyclohexane. This process is less preferred.

The low-monomer content polyisocyanates thus obtained are used as such or are dissolved in suitable solvents inert towards NCO groups to give polyisocyanate solutions. The polyisocyanates prepared by the process according to the invention are used in the known applications such as 2-component polyurethane coatings or in adhesives applications. The polyisocyanates thus obtained moreover serve as starting materials, as is known, for further derivatives prepared therefrom, such as blocked polyisocyanates or hydrophilized polyisocyanates.

The invention shall be illustrated in detail by the following examples.

In the following examples all % data refer to % by weight unless stated otherwise.

The determination of the NCO contents was carried out by titration according to DIN EN ISO 11909.

The residual monomer contents of IPDI were measured by gas chromatograph using internal standard according to DIN EN ISO 10283.

The viscosity measurements were carried out using a Physica MCR 51 rheometer from Anton Paar Germany GmbH (DE) according to DIN EN ISO 3219, unless stated otherwise.

The determination of the Hazen colour number is conducted to DIN EN 1557.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Preparation of the catalyst solution: a 40% strength solution of trimethylbenzylammonium hydroxide (Triton B) in methanol was diluted with n-butanol to an active ingredient content of 5%, based on Triton B.

Example 1

Continuous, Inventive

Isophorone diisocyanate was initially degassed. For this purpose, the IPDI was continuously metered into a degassing column. In the course of steam heating using 2.0 bar steam and a reduced pressure of 0.3 mbar, 10% of the amount used were removed as distillate and recycled, while the remainder was run off as bottom product into a receiver for use for the trimerisation.

For the trimerisation, the isophorone diisocyanate degassed as described was continuously metered into a cascade of 3 stirred reactors. Reactor 1 was maintained at a temperature of 95° C., and vessels 2 and 3 were regulated to 115° C. The metering rate was regulated so as to result in a residence time per reactor of 1 hour in each case. By continuously metered addition of catalyst solution which corresponded to approx. 80 ppm Triton B (active ingredient) based on the amount of isophorone diisocyanate introduced, the trimerisation was started in the first reactor. The catalyst amount was regulated such that the original NCO content of at least 37.0% declined to 32.5%. In the second reactor, catalyst solution, which corresponded to approx. 20 ppm Triton B (active ingredient) based on the amount of isophorone diisocyanate introduced, was likewise continuously metered in. The amount here was regulated such that the NCO content further declined to a content of 30.5% (degree of trimerisation: 17%) in the third reactor.

During the reaction period, dry nitrogen was continuously metered into reactor 1 via an immersed tube. The amount corresponded to 20% of the vessel volume per hour.

From the crude trimerisate thus obtained, the excess isophorone diisocyanate was subsequently removed by distillation. The crude trimerisate obtained from the reaction was fed into the second stage distillation. The first stage was a falling-film evaporator with pumped circulation and the second stage a thin-film evaporator. The distillation was carried out at 150-180° C. and a pressure of 0.1-10 mbar. Following preconcentration in the first distillation stage to an isophorone diisocyanate content of approx. 10%, the residual isophorone diisocyanate content after distillation was 0.5%. The resin obtained as bottom product of the distillation was dissolved in butyl acetate in a stirred vessel.

The 70% strength resin solution gave the following characteristic data: NCO content 11.9%, viscosity 600 mPas (23° C.), monomer content 0.35%, Hazen colour number 25.

The isophorone diisocyanate recovered in the distillation step was fed back into the reaction.

The temperature management of the exothermic trimerisation in the stirred tank cascade was carried out by input temperature, input rate, catalyst metering rate and external heating and cooling. The reaction can be carried out continuously over a time period of more than 12 months without cleaning downtime being required. Following assessment during plant downtime, the reactor inner walls had no significant coating.

Comparative Example 2

Continuous, Non-Inventive

The comparative example was run as described above in example 1 with the difference that reactor 1 was maintained at a temperature of 60° C. and vessels 2 and 3, during the trimerisation reaction, were maintained at a temperature between 65 and 75° C. by internal heat exchanger and external cooling. The metering rate of IPDI and the continuous metered addition of the catalyst solution in reactor 1 and 2 corresponded to the conditions described in example 1. The catalyst amount was regulated so that the original NCO content of at least 37% declined to a content of 30.5% (degree of trimerisation: 17%) in the third reactor. Since the catalyst was still active even in the 3rd reaction tank due to the relatively moderate reaction temperature, the IPDI trimer crude solution was stopped by addition of approximately 50% by weight of dibutyl phosphate (DBP), based on the Triton B catalyst used. During the reaction period, dry nitrogen was continuously metered into reactor 1 via an immersed tube as described in example 1.

The reaction was carried out continuously over a long time period. After a running time of 7 to 14 days, significantly reduced cooling performance was observed. Following assessment during plant downtime, the reactor inner walls and heat exchanger were heavily coated with solid deposits of polymeric polyisocyanate, and ammonium chloride as catalyst breakdown products. The plant has to be cleaned at regular, at least monthly, intervals.

Example 3

Batch, Inventive 1200 g of isophorone diisocyanate (IPDI) were charged in a multi-neck flask equipped with stirrer, reflux condenser, nitrogen inlet and vacuum connection and provision for metered addition of catalyst. The flask is degassed three times for 15 minutes at room temperature under reduced pressure (0.3 mbar) and filled each time with nitrogen ($N_2$). An oil bath is used for heating to an internal temperature of 95° C. under a gentle flow of $N_2$. Beginning at this temperature, the 5% strength catalyst solution (density 0.82 g/ml) is added dropwise at a metering rate of 15 ml/h. After approximately 10 minutes, the exothermic trimerisation reaction starts. The temperature increases to 110° C. and is maintained at this temperature by gentle cooling and subsequent heating. After 4 ml of the catalyst solution have been metered in (after 16 min), further metered addition is stopped. After 30 minutes, an NCO content of 32.4% is reached (degree of trimerisation 14%). A further 0.5 ml of catalyst solution (metering rate 3 ml/h) is metered in and, after a further 10 minutes, an NCO content of 31.7% ($T_g$=16%) is reached. For thermal stopping, the solution is further stirred for 30 minutes at 110-120° C. The crude solution is clear, with no turbidity and without any coating on the flask wall. For the reaction, 154 ppm Triton B (active ingredient) were used.

This crude clear solution obtained, having an NCO content of 31.6% ($T_g$=16%), is freed from monomeric IPDI in a two-stage continuous distillation using pre-evaporator and thin film evaporator at 180° C./0.14 mbar and a metering rate of the crude solution of 280 g/h. 206 g of polyisocyanate resin is obtained, which is dissolved in butyl acetate at 110° C. over a period of 2.5 h with stirring to give a 70% strength solution.

A 70% strength solution of IPDI trimerisate in butyl acetate is obtained having the following characteristic data: NCO content 11.8%, viscosity 610 mPas (23° C.), monomer content 0.13%, Hazen colour number 17.

Comparative Example 4

Batch, Low Reaction Temperature, Non-Inventive

As described in inventive example 3, 1200 g of IPDI are pretreated by degassing and filling with $N_2$ and heated to an internal temperature of 65° C. At this temperature, 4.5 ml of catalyst solution are metered in at a metering rate of 12 ml/h. The exothermic trimerisation reaction is maintained at a reaction temperature of 70-75° C. by repeated cooling. On reaching an NCO content of 30.7% ($T_g$=19%), 0.44 ml of a 25% strength solution of dibutyl phosphate in IPDI (density 1.05 g/ml) is added as stopper. The internal temperature falls, stirring is continued for 15 min at 80° C. and a cloudy crude solution is obtained having an NCO content of 29.8% ($T_g$=21%). For the reaction, 154 ppm Triton B (active ingredient) were used.

The cloudy crude solution is distilled as described in example 3 in the two-stage distillation with pre-evaporator/thin-film evaporator at 180° C./0.1 mbar and a metering rate of the crude solution of 370 g/h. The clear solid resin obtained is dissolved to 70% strength in butyl acetate, and a clear solution is obtained having the following characteristic data: NCO content 11.7%, viscosity 690 mPas (23° C.), monomer content 0.09%, Hazen colour number 30.

After distillation of the crude solution, a cloudy coating is found on the inner wall of the reaction flask.

Comparative Example 5

Batch, High Reaction Temperature, Non-Inventive

As described in inventive example 3, 300 g of IPDI are pretreated by degassing and filling with $N_2$ and heated to an internal temperature of 140° C. Starting at a metering rate of 2.0 ml/h, 0.5 ml (70 ppm Triton B) is initially added at 142° C. The metering rate is increased to 4.0 ml/h at 142-145° C. and in total 2.0 ml (280 ppm Triton B) is added. The NCO content falls only slightly to a value of 36.3%. For certainty, 1 ml of a 25% strength dibutyl phosphate solution in IPDI is added for stopping and the solution allowed to cool. Despite the almost double amount of catalyst, relative to inventive example 3 and comparative example 4, no trimerisation reaction occurs.

The invention claimed is:

1. A process for preparing a cycloaliphatic polyisocyanate containing isocyanurate groups comprising trimerizing a cycloaliphatic diisocyanate in the presence of a catalyst solution comprising at least one quaternary ammonium hydroxide in a reaction solution, wherein the catalyst solution is metered in to said reaction solution such that a reaction temperature greater than 90° C. and less than or equal to 140° C. is maintained.

2. The process of claim 1, wherein the catalyst solution is metered in to said reaction solution such that a reaction temperature greater than 90° C. and less than or equal to 135° C. is maintained.

3. The process of claim 1, wherein the catalyst solution is metered in to said reaction solution such that a reaction temperature greater than 90° C. and less than or equal to 120° C. is maintained.

4. The process of claim 1, wherein the process is carried out continuously in one or more stirred tanks.

5. The process of claim 1, wherein an isocyanate content is achieved corresponding to a degree of trimerisation of from 8 to 30%.

6. The process of claim 1, wherein an isocyanate content is achieved corresponding to a degree of trimerisation of from 12 to 24%.

7. A continuous process for preparing a cycloaliphatic polyisocyanate containing isocyanurate groups comprising trimerizing a cycloaliphatic diisocyanate in the presence of a catalyst solution comprising at least one quaternary ammonium hydroxide in a stirred tank cascade with n stirred tanks, wherein, in at least n/2 or (n/2−0.5) tanks, the metered addition is such that the reaction temperature in at least n/2 or (n/2+0.5) tanks is greater than 90° C. and less than or equal to 140° C., where n/2 applies to an even number of tanks and (n/2−0.5) or (n/2+0.5) applies to an odd number of tanks and n is a whole number from 2 to 6.

8. The process of claim 7, wherein an isocyanate content is achieved in the nth tank corresponding to a degree of trimerisation of from 8 to 30%.

9. The process of claim 7, wherein an isocyanate content is achieved in the nth tank corresponding to a degree of trimerisation of from 12 to 24%.

10. The process of claim 1, wherein the catalyst comprises from 0.001 to 2% by weight of quaternary ammonium hydroxide, based on the amount of diisocyanate.

11. The process of claim 1, wherein the catalyst comprises from 0.005 to 1% by weight of quaternary ammonium hydroxide, based on the amount of diisocyanate.

12. The process of claim 1, wherein the catalyst solution has a catalyst concentration of from 0.1 to 10% by weight, based on the catalyst solution.

13. The process of claim 1, wherein the catalyst solution has a catalyst concentration of from 0.2 to 8% by weight, based on the catalyst solution.

14. The process of claim 1, wherein the catalyst solution comprises at least one quaternary tetraalkylammonium hydroxide and/or a mixed quaternary tetraalkyl/aralkylammonium hydroxide and/or a quaternary tetraaralkylammonium hydroxide.

15. The process of claim 1, wherein the catalyst solution comprises at least one quaternary trialkylaralkylammonium hydroxide.

16. The process of claim 14, wherein the catalyst solution comprises at least one quaternary tetraalkylammonium hydroxide and/or one quaternary mixed tetraalkyl/aralkylammonium hydroxide, wherein the alkyl groups of said at least one quaternary tetraalkylammonium hydroxide and/or one quaternary mixed tetraalkyl/aralkylammonium hydroxide are not substituted with any hydroxyl groups.

17. The process of claim 14, wherein the catalyst solution comprises a quaternary benzyltrialkylammonium hydroxide.

18. The process of claim 14, wherein the catalyst solution comprises benzyltrimethylammonium hydroxide.

19. The process of claim 1, wherein the cycloaliphatic diisocyanate comprises isophorone diisocyanate.

20. The process of claim 1, wherein the trimerization is stopped chemically or thermally.

21. The process of claim 20, wherein the trimerization is stopped chemically by adding an acidic compound, an acid, and/or an alkylating agent to the reaction solution.

22. The process of claim 1, further comprising, in a downstream step, removing residual monomeric cycloaliphatic diisocyanate from the polyisocyanate by distillation.

23. The process of claim 1, wherein the trimerization is stopped thermally.

* * * * *